United States Patent
Praame et al.

(10) Patent No.: US 10,517,754 B2
(45) Date of Patent: Dec. 31, 2019

(54) OSTOMY WAFER

(71) Applicant: Coloplast A/S, Humlebaek (DK)

(72) Inventors: Martin Praame, Svedala (SE); Rene Ferm Nyberg, Hilleroed (DK); Richard Morgan Hickmott, Helsingoer (DK); Jakob Bendix, Koebenhavn V (DK)

(73) Assignee: Coloplast A/S, Humlebaek (DK)

( * ) Notice: Subject to any disclaimer, the term of this patent is extended or adjusted under 35 U.S.C. 154(b) by 407 days.

(21) Appl. No.: 15/313,980

(22) PCT Filed: May 28, 2015

(86) PCT No.: PCT/DK2015/050135
§ 371 (c)(1),
(2) Date: Nov. 25, 2016

(87) PCT Pub. No.: WO2015/180732
PCT Pub. Date: Dec. 3, 2015

(65) Prior Publication Data
US 2017/0143535 A1  May 25, 2017

(30) Foreign Application Priority Data

May 28, 2014 (DK) .................................. 2014 70310

(51) Int. Cl.
*A61F 5/445* (2006.01)
*A61F 5/443* (2006.01)

(52) U.S. Cl.
CPC .............. *A61F 5/445* (2013.01); *A61F 5/443* (2013.01)

(58) Field of Classification Search
CPC combination set(s) only.
See application file for complete search history.

(56) References Cited

U.S. PATENT DOCUMENTS

| 4,762,738 A | * | 8/1988 | Keyes ..................... A61F 5/445 |
| | | | 428/34.3 |
| 5,386,835 A | * | 2/1995 | Elphick ................. A61F 15/004 |
| | | | 128/846 |
| 5,636,643 A | * | 6/1997 | Argenta .............. A61M 1/0088 |
| | | | 128/897 |

(Continued)

FOREIGN PATENT DOCUMENTS

| EP | 0882437 A2 | 12/1998 |
| EP | 0882437 A3 | 12/1998 |

(Continued)

*Primary Examiner* — Tatyana Zalukaeva
*Assistant Examiner* — Guy K Townsend
(74) *Attorney, Agent, or Firm* — Coloplast Corp., Coloplast A/S; Nick Baumann (57) ABSTRACT

An ostomy wafer includes a stoma receiving hole formed through an adhesive layer and a backing layer of the ostomy wafer and has a central area formed as a continuous band of material around an entire perimeter of the stoma receiving hole. An outer periphery of the wafer is formed by a plurality of petals connected to and extending away from the central area, and a plurality of bridges is provided formed between adjacent petals of the plurality of petals. A thickness of the adhesive layer measured within one of the plurality of bridges is greater than a thickness of the adhesive layer measured within one of the plurality of petals.

13 Claims, 4 Drawing Sheets

(56) References Cited

U.S. PATENT DOCUMENTS

| | | | |
|---|---|---|---|
| 6,099,508 A * | 8/2000 | Bousquet | A61M 39/0247 128/DIG. 26 |
| D433,140 S | 10/2000 | Nielsen | |
| 7,049,073 B2 * | 5/2006 | Chernov | C07F 9/2408 435/174 |
| 7,049,478 B1 | 5/2006 | Smith | |
| 7,708,724 B2 * | 5/2010 | Weston | A61M 1/0088 604/304 |
| 8,211,073 B2 * | 7/2012 | Dove | A61F 5/445 604/332 |
| 8,409,157 B2 * | 4/2013 | Haggstrom | A61M 1/0031 604/307 |
| 8,409,158 B2 * | 4/2013 | Edvardsen | A61F 5/4404 604/100.01 |
| 8,734,410 B2 * | 5/2014 | Hall | A61M 1/0084 604/319 |
| 8,758,314 B2 * | 6/2014 | Hall | A61F 5/445 604/319 |
| 8,771,243 B2 * | 7/2014 | Khan | A61F 5/449 604/290 |
| 9,078,990 B1 * | 7/2015 | Obst | A61M 27/00 |
| 9,622,903 B2 * | 4/2017 | Israelson | A61F 5/443 |
| 2006/0195053 A1 * | 8/2006 | Oelund | A61F 5/443 602/43 |
| 2007/0066946 A1 * | 3/2007 | Haggstrom | A61M 1/0031 604/313 |
| 2008/0161778 A1 * | 7/2008 | Steward | A61M 1/0088 604/543 |
| 2008/0287892 A1 * | 11/2008 | Khan | A61F 5/449 604/313 |
| 2009/0131893 A1 * | 5/2009 | Priest | A61F 5/4408 604/342 |
| 2009/0192467 A1 * | 7/2009 | Hansen | A61B 17/3462 604/174 |
| 2009/0209917 A1 * | 8/2009 | Tanaka | A61K 9/007 604/174 |
| 2009/0299388 A1 | 12/2009 | Barker et al. | |
| 2010/0022933 A1 * | 1/2010 | Oelund | A61F 5/443 602/54 |
| 2010/0145293 A1 * | 6/2010 | Verhaalen | A61F 5/445 604/337 |
| 2010/0168693 A1 * | 7/2010 | Edvardsen | A61F 5/44 604/355 |
| 2010/0262095 A1 * | 10/2010 | Hall | A61M 1/0084 604/319 |
| 2010/0280468 A1 * | 11/2010 | Haggstrom | A61M 1/0031 604/318 |
| 2012/0101458 A1 * | 4/2012 | Hall | A61F 5/445 604/319 |
| 2012/0143154 A1 * | 6/2012 | Edvardsen | A61F 5/4404 604/318 |
| 2012/0143155 A1 * | 6/2012 | Edvardsen | A61F 5/4404 604/318 |
| 2013/0138063 A1 | 5/2013 | Wiltshire et al. | |
| 2013/0338613 A1 * | 12/2013 | Haggstrom | A61M 1/0031 604/315 |
| 2014/0114265 A1 * | 4/2014 | Israelson | A61F 5/443 604/342 |
| 2014/0309601 A1 * | 10/2014 | Hall | A61F 5/445 604/319 |
| 2016/0120687 A1 * | 5/2016 | Obst | A61F 5/443 604/337 |
| 2017/0143535 A1 * | 5/2017 | Praame | A61F 5/445 |
| 2017/0224523 A1 * | 8/2017 | Bendix | A61F 5/445 |
| 2018/0021164 A1 * | 1/2018 | Fenton | A61F 5/445 604/336 |
| 2018/0021165 A1 * | 1/2018 | Fenton | A61F 5/445 604/338 |
| 2018/0104089 A1 * | 4/2018 | Nyberg | A61F 5/445 |
| 2018/0235801 A1 * | 8/2018 | Oellgaard | A61F 5/4404 |

FOREIGN PATENT DOCUMENTS

| | | |
|---|---|---|
| EP | 1053725 B1 | 4/2005 |
| EP | 1541180 B | 7/2010 |
| GB | 2311467 A1 | 10/1997 |
| WO | 08031411 A1 | 3/2008 |
| WO | 2009/006901 A1 | 1/2009 |
| WO | 12150235 A1 | 11/2012 |

* cited by examiner

OSTOMY WAFER

The invention relates to an ostomy wafer for use in an ostomy appliance, in particular, the invention relates to ostomy wafers for ostomies or stomas located on a bulge or hernia on the skin surface of a user.

BACKGROUND

In connection with surgery for a number of diseases in the gastro-intestinal tract, one of the consequences in many cases is that the patient is left with an abdominal stoma, such as a colostomy, an ileostomy or a urostomy in the abdominal wall for the discharge of visceral contents. The discharge of visceral contents cannot be regulated at will. For that purpose, the user will have to rely on an appliance to collect the material emerging from such opening in a bag, which is later emptied and/or discarded at a suitable time.

An ostomy appliance may be in the form of a one-piece appliance for which a collecting bag for human body wastes is permanently, or fixedly, secured to an adhesive wafer for attachment to the human skin. Alternatively, the ostomy appliance may be a two-piece appliance comprising a wafer and a collecting bag which may be coupled to and uncoupled from each other through a coupling means. This has the effect that the wafer does not need to be separated from the skin of the user as often as exchange of the collecting bag requires. The wafer may need only to be changed for example every third or fourth day depending on the user, whereas the collecting bag may be changed more than once per day. Typically, it is desirable to need as few exchanges of the wafer as possible in order to reduce the risk of skin complications.

One of the main concerns of ostomates using ostomy appliances having an adhesive wafer for attachment to the skin surrounding a stoma, and where a collecting bag is attached to the wafer for collecting stoma output, is that the ostomy adhesive attachment may be compromised resulting in leakage or even complete detachment of the ostomy appliance.

Numerous attempts have been made to solve this problem and even though some attempts have been partly successful, still there exist no products which completely solve this problem.

One reason why this is so difficult to solve is the fact that stomas and peoples anatomy are very different. Different considerations need to be made for thin people than for larger people, for different skin types, for placement of the stoma which may vary a lot from person to person, for scar tissue surrounding the stoma, for local irregular skin topography and combinations of all of the above.

Particularly in relation to persons suffering from hernia, i.e. the phenomenon that a bodily structure (e.g. the intestine) protrudes through a rupture in smooth muscle tissue surrounding it, experience shows that it is often very difficult to attach an ostomy appliance to the skin surface where the hernia is located in a manner that provides satisfactory protection against leakage from stomal fluids. It is not uncommon that the surgical procedure undertaken to make a stoma on a patient also results in a weakening of the muscle tissue of the stomach wall which may consequently lead to the formation of a hernia where the stoma is located on the skin surface (or close or adjacent to the stoma).

Moreover, a hernia is not a static phenomenon. It is almost certain never to take a perfect geometrical shape but instead often has a highly irregular topography. This may be caused by many factors such as conditions in the physical surroundings of the user, level of activity of the user and contents of the bowels at any given time, just to mention a few.

In addition to the formation of hernias, other physical conditions or pathologies may also mean or lead to irregular skin topography such as bulges or otherwise "hilly" stomach skin surface, the causes including e.g. trauma and/or obesity.

DESCRIPTION OF RELATED ART

GB2311467 describes an ostomy appliance comprising a collection pouch and an adhesive flange coupled to the pouch for securing the appliance with respect to the skin of a wearer. The adhesive flange has an aperture which communicates with an interior of the pouch and the flange comprises a plurality of fingers which extend away from the aperture. The document also describes an adhesive flange for an ostomy appliance.

Wafers with a flower shaped outline such as disclosed in GB2311467 may more easily be fitted around a bulgy stoma due to the fingers. However, in the part of the outline connecting the fingers, wrinkles and folds may occur when fitted to curved surfaces. If such wrinkles become too large, they may give rise to leakage and discomfort for the user.

SUMMARY OF THE INVENTION

The present invention provides an adhesive wafer to be used as part of or with an ostomy appliance. Particularly, the invention provides a solution to minimize the risk of leakage under the wafer when applied to an irregular or bulgy skin area. The wafer is especially advantageous to be used on users suffering from and having their stoma located on a non-planar and non-regular skin surface.

DETAILED DESCRIPTION OF THE INVENTION

For interpretations in the context of the present application, some definitions regarding the subject matter of the attached claims are presented below.

When referring to the proximal side of a device or part of a device, the referral is to the skin-facing side, when the ostomy appliance is worn by a user. Likewise whenever referring to the distal side of a device or part of a device, the referral is to the side facing away from the skin, when the ostomy appliance is worn by a user. In other words, the proximal side is the side closest to the user, when the appliance is fitted on a user and the distal side is the opposite side—the side furthest away from the user in use.

The axial direction, or axially, is defined as the direction of the stoma when the appliance is worn by a user. Thus the axial direction is substantially perpendicular to the abdominal surface of the user.

The radial direction, or radially, is defined as transverse to the axial direction that is transversely to the direction of the stoma.

"Release liner" is intended to define a liner covering the proximal (skin contacting) side of the skin-friendly adhesive, that ensures at least that the properties of the adhesive are preserved and that the adhesive surface is not laid open until just before the use.

"Peristomal skin surface" is intended to define an area of the skin surface adjacent to and surrounding the stoma. The extent of the area may be considered to correspond approximately to a skin surface area covered by at least a first section of the ostomy wafer—the first section then being closer to the stoma than a second section.

"Petal" is intended to define a portion of the wafer extending radially from the central area of the wafer, like the petals of a flower. The petals act as fingers or flaps that can be fitted around a protruding body part. The petal may end in an apex being rounded, angular or pointy.

"Bridge" is intended to define the part of the wafer connecting two neighboring petals.

By "center" or "central" is addressed the stoma receiving hole or the area surrounding the hole. I case the wafer is symmetric the center will be equal to the mathematically defined center. However, asymmetric wafers may occur, having the hole placed eccentric with regard to the mathematically defined center.

By "convex" is herein meant a curved line arching away from point of origin. Thus, the start point and the end point of the line is closer to the point of origin than the middle portion of the line. In the same way is "concave" defined as a line arching towards the point of origin. If nothing else is stated, the point of origin is the central area/stoma receiving hole of the wafer.

"Wrinkle" is here intended to define the situation where the adhesive deforms on the top film side, but remains in contact with the skin. Thus, the adhesive is fully attached to the skin but seen from the distal side, the top film may look wrinkled.

"Fold" is here intended to define the situation where the adhesive loses contact with the skin, i.e. detaches from the skin.

"Embossed lines" is here defining a pattern of lines being embossed into the adhesive from the distal surface of the wafer. Thus, the skin-contacting surface of the wafer is continuous and not embossed whereas the non-skin-facing surface of the wafer appears with an indented pattern.

In a first aspect, the invention relates to an ostomy wafer comprising:

a stoma receiving hole formed at a center of the wafer and a central area formed as a continuous band of material around the stoma receiving hole;

an outer periphery of the wafer is formed by a plurality of petals extending away from the central area; and a plurality of bridges, each bridge formed between adjacent petals of the plurality of petals, wherein the thickness of the bridges is higher than the thickness of the petals and the bridges are provided with an embossed pattern of lines.

When an ostomy wafer conforms to the curvature of a body, the wafer may need to fold (where the adhesive loses contact with the skin) or wrinkle (where the adhesive deforms on the top film side, but remains in contact with the skin) in order to compress sufficiently. Depending on several factors (adhesive type, skin properties, local body shape, etc.) this compression might be focused to a few points along the edge. Seen from the distal surface it may be difficult for the user to distinguish between wrinkles and fold.

Providing the bridges with embossed lines may facilitate that wrinkles naturally occurring in the bridge region when the wafer is mounted on a curved surface will follow the embossed lines. Moreover, the layer of adhesive being thicker in this region renders it possible that the wrinkles may be absorbed by the adhesive and never turn into profound folds. Such folds may develop into leakage channels. The embossed lines pattern may prevent this from happening during application of the wafer by the way it is guiding the material towards a distributed compression, resulting in several wrinkles, rather than the localized compression, resulting in folds.

The adhesive at the edge portion may be a pressure sensitive adhesive. The adhesive may be soft and slightly plastic/moldable in order to better contain and absorb the wrinkles that may occur during application to the skin. A thicker layer of adhesive is more capable of absorbing the wrinkles than a thin layer.

The wafer may comprise at least one adhesive. In embodiments, the wafer may comprise two or more adhesives, for example a first adhesive at the central portion and a second adhesive at the edge portion. This disposition of the first and second adhesive effectively provides an ostomy base plate wherein the first adhesive having one set of characteristics covers the peristomal area, and the second adhesive having another set of characteristics covers the skin surface around (radially beyond) the peristomal skin surface.

In embodiments, the adhesive may comprise a skin-friendly pressure sensitive adhesive composition suitable for medical purposes comprising a rubbery elastomeric base and one or more water soluble or water swellable hydrocolloids, the adhesive composition comprising a substantially homogeneous mixture of 25-60% of one or more polyisobutylenes, 3-35% of one or more styrene copolymers, and 20-60% of one or more hydrocolloids, wherein the percentage by weight of one or more polyisobutylenes and one or more styrene copolymers and one or more hydrocolloids add up to 100% by weight of the adhesive composition. For further information on such compositions reference is made to applicant's granted European patent EP1541180B1.

In embodiments, the adhesive is elastic. The second adhesive may be more or may be less elastic than the first adhesive or the two adhesives may even have identical elasticities if desired.

In embodiments, the adhesive comprises a polar plasticising oil or a combination of polar plasticising oils in the content of above 10% (w/w) of the final adhesive, and at least one polar polyethylene copolymer, wherein the content of the polyethylene copolymer is 10-50% (w/w) of the final adhesive, the polyethylene copolymer has a melt flow index below 2 g/10 min (190° C./21.1N).

In embodiments, polymers that may be used for the adhesive may be copolymers of ethylene and a polar monomer. The copolymers typically comprise less than about 70% ethylene, have water vapor transmission of more than 50 g/m2/day and a melt flow index of less than 2 g/10 min (190° C./21.1N). The melt flow index can be measured by the methods given in ISO 1133 and ASTM D1238. Examples of such polymers are copolymers of ethylene and vinyl acetate and copolymers of ethylene and butyl acrylate. Particularly preferred is ethylene and vinyl acetate copolymers with more than about 40% (w/w) vinyl acetate, a melt flow index of less than 2 g/10 min (190° C./21.1N), and a water vapor transmission of more than 50 g/m2/day for a 150 μm sheet when measured according to MVTR Test Method (inverted cup method).

In embodiments, the adhesive may comprise polar oils, generally being those that have good solubility in the polar domains of the polymer, i.e. provide softness without sacrificing too much tensile strength of the polymer. Oils that can support good water vapor permeability are preferred. Examples of such oils are vegetable and animal oils and derivatives thereof. Preferred polar oils are esters, ethers and glycols and particularly preferred is Poly Propylene Oxide, e.g. alpha-butoxy-polyoxypropylene. Further information on the types of adhesives suitable for the adhesive disclosed in these embodiments is available in applicant's published application WO 2009/006901A1.

The enhanced thickness of the bridges may be achieved by a thicker layer of adhesive. Whereas one would expect a smaller thickness of the bridge would result in creation of smaller/less wrinkles/folds, it has surprisingly been shown that a thicker layer of material in the bridge area may be better able to "absorb" the wrinkle by compacting the material instead of creating a proper fold.

In addition, the evenly distributed deformation promotes better adhesion during wear, as there are fewer stress concentrations in the wafer.

In some cases, wrinkles occur naturally, but in a random pattern of wrinkles. This pattern can be experienced as distressing by the user, since wrinkles can be experienced as a pre-cursors to leakage. By controlling the wrinkles with the embossed lines pattern, the wafer, when applied may look very similar to how it looks before application and the user is thus relieved of potential concern.

The embossed lines of the wafer may be provided essentially where fold lines would naturally occur in when the wafer is fitted over a protruding body part. The embossed lines facilitate better control of folding/wrinkling of the wafer.

The tactility of the embossed lines pattern may draw attention to the area during the application, and may encourage the user to spend more time pressing down the edges in this area and make application of the wafer easier.

The petals may also be provided with embossed lines such that the entire edge of the wafer is provided with embossed lines. The distance between the embossed lines may be larger at the petals than at the bridge.

The petals may have a convex apex and the bridges may define a concave shape between the petals.

The wafer may be provided with at least three petals, such as at least four petals, five petals or even at least six petals.

All of the petals may have the same length or the petal length may vary.

Each of the plurality of petals has a petal length measured from the stoma receiving hole to an apex of the petal and the bridge has a bridge length measured from the stoma receiving hole to an apex of the bridge, with the bridge length may be less than the petal length.

The radially extending petals may be spaced apart equidistantly around the circumference of the center area.

A user having a stoma located on a bulge or hernia, or on an otherwise "hilly" topographic skin surface may achieve improved control of the wafer application procedure by the present invention.

The skin facing adhesive layer of the ostomy wafer may comprise any suitable adhesive. The adhesive may comprise absorbent particles such as hydrocolloids. The distal surface of the wafer may be provided with a backing layer.

The central area of the wafer may comprise second adhesive being different from the first adhesive of the wafer.

The embossed lines may extend from the edge portion of the wafer and towards the center. The embossed lines have an inner end proximal to the center of the wafer and an outer end at the edge of the wafer. The embossed lines thereby defines a band of embossed lines along at least a part of the edge portion of the wafer. The portion of the bridge being provided with embossed lines may be sickle-shaped.

The embossed lines at the bridge may be substantially parallel and thus not strictly in radial direction. The distance between the lines may be substantially the same for the lines in the middle of the bridge whereas the distance between the lines may decrease when moving towards the petals.

Figure 1:
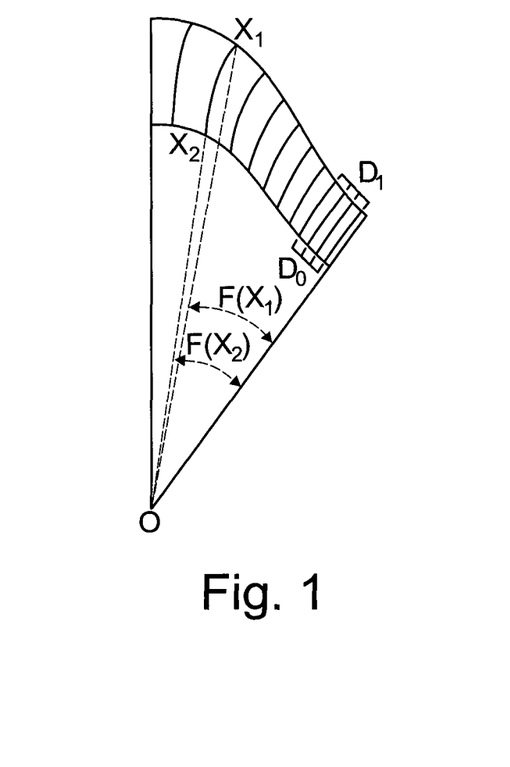
FIG. 1 is a schematic view of a segment of a wafer according to the invention

The embossed lines may be according to the following cubic equation:

$$F(x)=ax3+bx2+cx+d$$

where x is the number of embossed lines (Xn) counted from the bridge region and F(x) is the angles from the line between center (O) and inner or outer end of the correlating embossed line to the line going from center (O) to bridge, see FIG. 1. All measures are I millimeters unless otherwise stated.

In one embodiment the angle from the line between wafer center (O) and inner end of an embossed line is defined by a cubic equation F(x), which is limited in the following way:

$$G1(x) \leq F(x) \leq G2(x),$$

where $$F(x)=ax3+bx2+cx+d$$

and $$G1(x)=a1x3+b1x2+c1x+d1$$

and $$G2(x)=a2x3+b2x2+c2x+d2.$$

Inner Points:
a1=0.2≤a≤a2=0.3 e.g. a=0.242 and
b1=−0.13≤b≤b2=−0.09 e.g. b=−0.104 and
c1=3≤c≤c2=3.4 e.g. c=3.18 and
d1=6≤d≤d2=9 e.g. d=7.82
for example F(x)=0.242x3−0.104x2+3.18x+7.82
Outer Points In one embodiment the angle from the line between wafer center (O) and inner starting point of an embossed line is defined by a cubic equation F(x), which is limited in the following way:

$$G1(x) \leq F(x) \leq G2(x)$$

where $$F(x)=ax3+bx2+cs+d$$

and $$G1(x)=a1x3+b1x2+c1x+d1$$

and $$G2(x)=a2x3+b2x2+c2x+d2$$

In one embodiment;
a1=0.045≤a≤a2=0.075 e.g. a=0.0503 and
b1=−0.6≤b≤b2=−0.3 e.g. b=−0.356 and
c1=3≤c≤c2=4.5 e.g. c=3.60 and $d1=5\leq d\leq d2=7$ e.g. $d=6.53$ For example $F(x)=0.0503x3-0.356x2+3.60x+6.53$ The embossed lines may be distributed according to the above equation, but with the exemption of the 2-5 innermost embossed lines. These lines may be distributed with equal spacing.

In one embodiment the inner distance (Di) may be between 1.60 mm and 1.80 mm such as between 1.65 mm and 1.75 mm or even 1.70 mm, and the outer distance (Do) may be between 1.70 mm and 1.90 mm, such as between 1.75 mm and 1.85 mm or even 1.80 mm.

In one embodiment the number of inner embossed lines with equal spacing is dependent on the diameter of the circumscribed circle. E.g. a diameter A of 117 mm may give an amount of inner embossed lines of three, e.g. a diameter of 126 mm may give an amount inner embossed lines of three and a half (the center embossed lines may be shared by two adjacent embossed lines patterns), and e.g. a diameter of 135 mm may give an amount of four.

Figure 2:
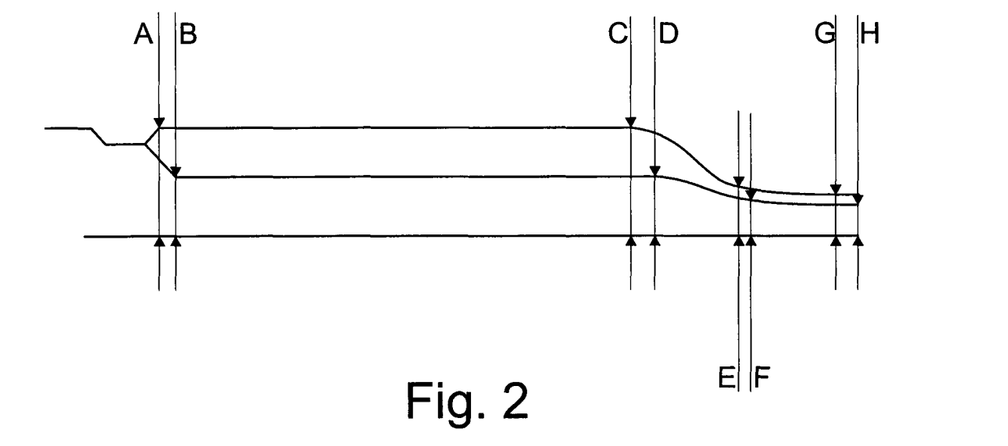
FIG. 2 is a cross section of a bridge of an embodiment of the invention

The height of the embossed lines is defined in a cross sectional view by four measures on the top surface and four in the groove surface, see FIG. 2 showing a cross-section of the bridge. These measures vary from bridge to the petal apex. The embossed lines are in the form of lines depressed in the adhesive, thereby defining valleys (lowest point in the lines and ribs (highest point between lines).

A defines the height of the ribs at the inner end of the embossed lines,

B defines the height of the valleys at the inner end of the embossed lines,

C defines the height of the ribs at the outer end of the embossed lines,

D defines the height of the ribs at the outer end of the embossed lines,

E and G defines the height of the ribs at the edge and

F and H defines the height of the valleys at the edge.

The measures in the bridge may for example be as follows:

A is between 0.6 mm and 3 mm e.g. 1.4 mm, B is between 0.3 mm and 2.5 mm e.g. 0.8 mm, C is between 0.6 mm and 3 mm e.g. 1.4 mm, D is between 0.3 mm and 2.5 mm e.g. 0.8 mm, E is between 0.2 mm and 2 mm e.g. 0.6 mm, F is between 0.2 mm and 1.5 mm e.g. 0.45 mm, G is between 0.2 mm and 1 mm e.g. 0.4 mm, and H is between 0.2 mm and 1 mm e.g. 0.3 mm.

The measures in the petal apex may for example be as follows:

A is between 0.6 mm and 3 mm e.g. 1 mm, B is between 0.3 mm and 2 mm e.g. 0.8 mm, C is between 0.6 mm and 3 mm e.g. 0.75 mm, D is between 0.3 mm and 2 mm e.g. 0.6 mm, E is between 0.2 mm and 1 mm e.g. 0.6 mm, F is between 0.2 mm and 1 mm e.g. 0.45 mm, G is between 0.2 mm and 1 mm e.g. 0.4 mm, and H is between 0.2 mm and 1 mm e.g. 0.3 mm.

The wafer may be provided with coupling means for attaching a collection bag to the wafer (two-piece device) or a collection bag may be permanently attached to the wafer (one-piece device).

During use, the collecting bag is secured to the adhesive wafer. Thus in one embodiment, the ostomy appliance is a one-piece ostomy appliance in which the collecting bag is permanently secured to the adhesive wafer, for example by adhesive or welding. In the latter embodiment, the collecting bag may be integrated with the wafer.

In another embodiment, the collecting bag and the adhesive wafer form a two-piece ostomy appliance which is delivered to the user in two pieces that must be connected to each other by the user. The collecting bag may be secured to the adhesive wafer by means of an adhesive provided between the collecting bag and the adhesive wafer. The latter adhesive may be provided on the opposite side of the adhesive wafer than the skin facing adhesive layer. Alternatively, or as a supplement, the collecting bag may be coupled to the adhesive wafer by means of a mechanical coupling means.

The shape of the central area of the adhesive wafer may substantially round such as circular or oval or it may have a shape reflecting the outline of the wafer, with tongues extending towards the petals.

The skin facing adhesive layer may be covered by a release liner. The release liner may be siliconised or otherwise provided with a non-stick surface on the side which faces the skin facing adhesive layer. The release liner may be in one piece or it may be in two or more pieces, facilitating stepwise application. This release liner must be removed in order for the user to adhere the skin facing adhesive layer to the skin of the user and does not form a part of the invention.

The edge portion of the wafer may be beveled in order to provide a smooth transition to the skin and avoid rolling up of the edges.

DETAILED DESCRIPTION OF THE DRAWING

Initially, it shall be noted that the figures are schematic illustrations intended only to address the principles and functions of the wafer according to the invention and are not to be considered limiting to the scope of the attached claims. Furthermore, the figures and particularly the individually illustrated elements are not necessarily to scale, neither individually nor in relation to each other.

Figure 3:
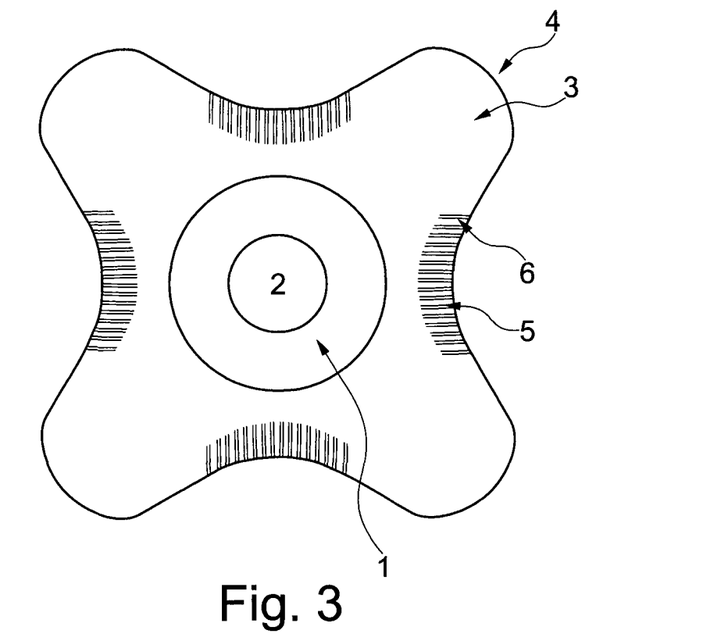
FIG. 3 is a top view of one embodiment of the invention

FIG. 3 shows a schematic view of an ostomy wafer according to the invention, seen from the skin-facing side. The wafer comprises a central portion 1 surrounding a stoma receiving hole 2. From the central portion 1 are radially extending petals 3 having a convex apex 4, and connecting neighboring petals are bridges 5. The bridges are provided with embossed lines 6 being substantially parallel and with uniform distance between the lines.

Figure 4:
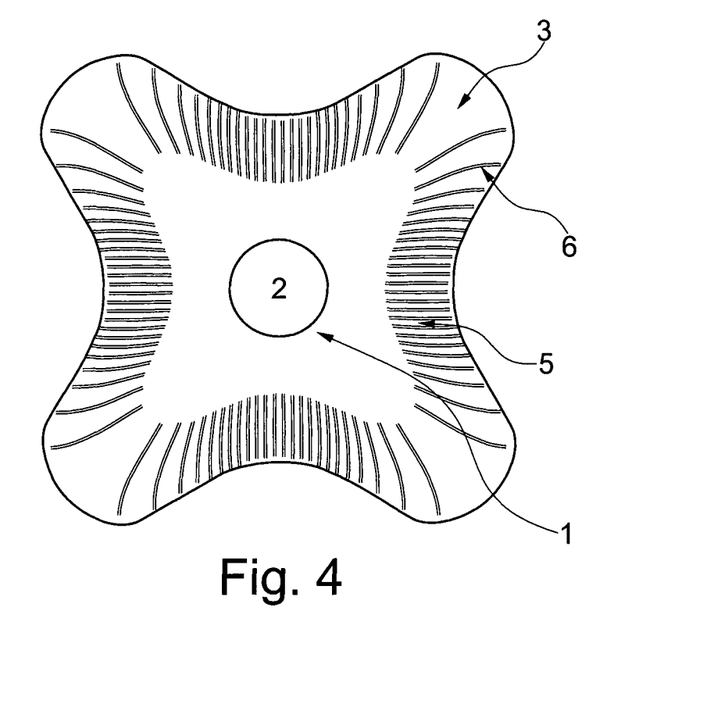
FIG. 4 is a top view of another embodiment of the invention

In FIG. 4 is shown another embodiment of the invention where the entire edge portion of the wafer is provided with embossed lines. The bridge is provided with substantially parallel lines as in FIG. 1, whereas the petals have less lines, and the lines may be curved.

Figure 5:
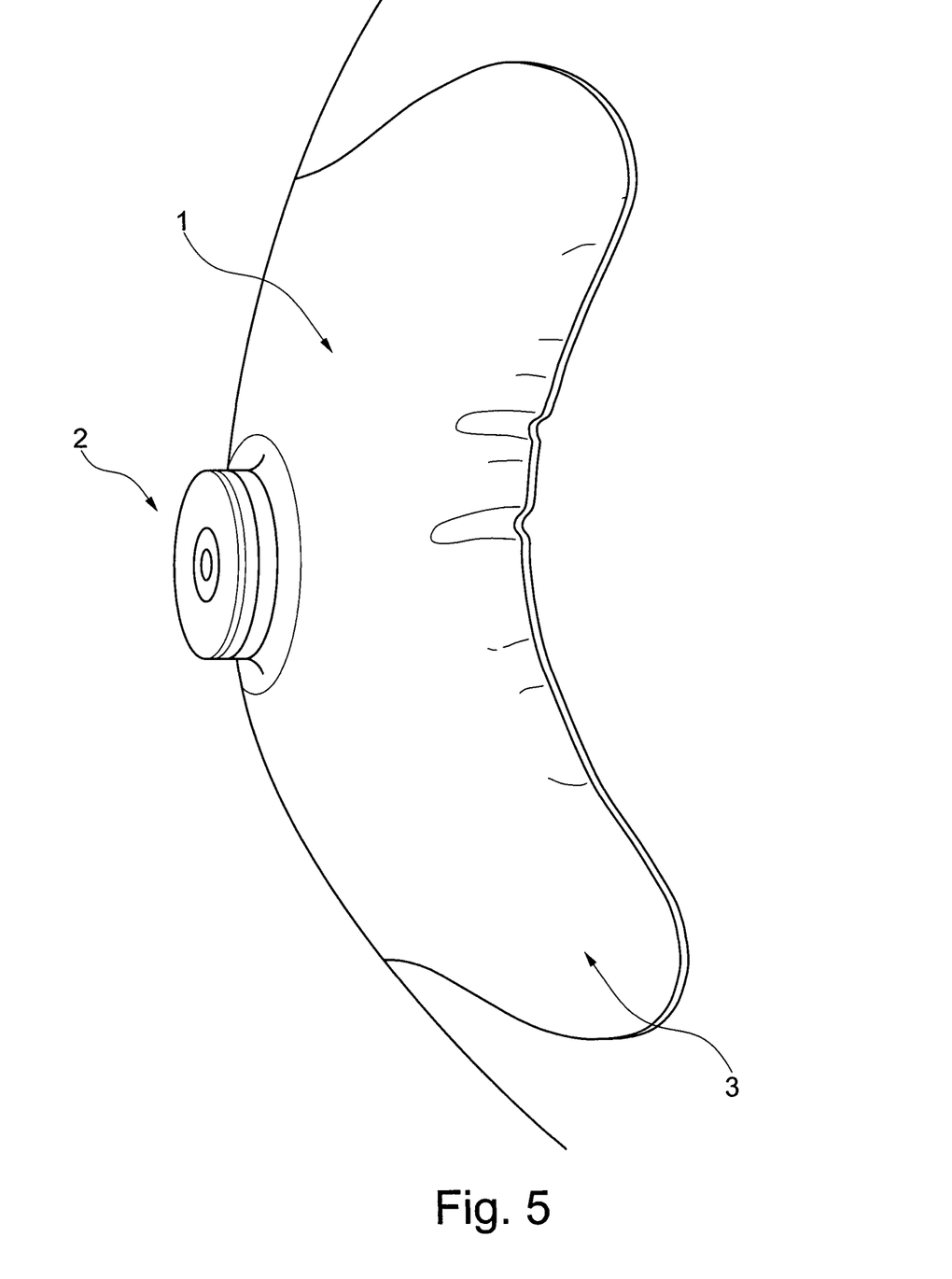
FIG. 5 is a close up photo of the bridge portion of a wafer without embossed lines and FIG. 6 is a close up view of the bridge portion of an embodiment of the invention.

FIG. 5 shows a wafer without embossed pattern of lines after application to a curved surface. As can be seen, the bridge develops folds, providing channels for leakage.

Figure 6:
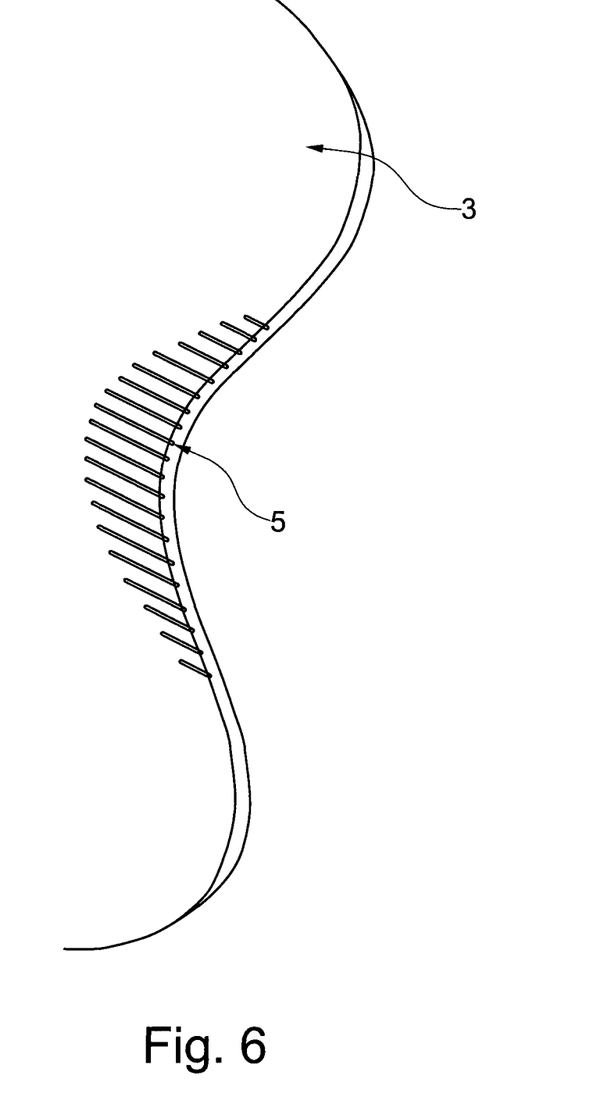

FIG. 6 show the bridge of an embodiment of the present invention after application to the same curved surface as in FIG. 5. As can be seen, no wrinkles or fold occur.

The invention claimed is:

1. An ostomy wafer comprising:
a stoma receiving hole formed through an adhesive layer and a backing layer of the ostomy wafer and a central area formed as a continuous band of material around an entire perimeter of the stoma receiving hole;
a plurality of petals connected to and extending away from the central area, with each of the plurality of petals radially extending from the central area to an end that is formed as a convex apex; and
a plurality of bridges, each of the plurality of bridges formed between adjacent petals of the plurality of petals such that a first portion of an outer periphery of the wafer is concave and formed by one of the plurality of bridges;

wherein a thickness of the adhesive layer measured within one of the plurality of bridges is greater than a thickness of the adhesive layer measured within one of the plurality of petals and each of the plurality of bridges has an embossed pattern of lines formed in a surface of each of the plurality of bridges, wherein a distance between adjacent lines in the embossed pattern of lines increases in a direction from a location within each of the plurality of bridges toward one of the adjacent petals of the plurality of petals.

2. The ostomy wafer of claim 1, wherein an entire outer periphery of the wafer is provided with embossed lines.

3. The ostomy wafer of claim 1, wherein the embossed pattern of lines is an embossed pattern of radially extending lines.

4. The ostomy wafer of claim 1, wherein the central area is one of a circular area and an oval area.

5. The ostomy wafer of claim 1, wherein the plurality of petals comprises at least three petals.

6. The ostomy wafer of claim 1, wherein the plurality of petals comprises at least five petals.

7. The ostomy wafer of claim 1, wherein each of the plurality of petals is equidistantly spaced apart around a circumference of the central area.

8. The ostomy wafer of claim 1, wherein the embossed pattern of lines is an embossed pattern of parallel lines.

9. The ostomy wafer of claim 1, wherein each of the plurality of bridges has the embossed pattern of lines formed in the backing layer of the ostomy wafer.

10. An ostomy wafer comprising:

an adhesive layer applied to a backing layer, with a stoma receiving hole formed through the adhesive layer and the backing layer, with a central area of the ostomy wafer formed as a continuous band of material around an entire perimeter of the stoma receiving hole;

a first petal connected to and extending in a radial direction away from the central area, a second petal connected to and extending in a radial direction away from the central area, and a bridge connected between the first petal and the second petal, with each of the first petal and the second petal terminating at a convex apex and the bridge has an outermost radial edge connected between the first petal and the second petal that is concave; and an embossed pattern of lines formed in the backing layer of the bridge, with the embossed pattern of lines formed into a portion of the adhesive layer;

wherein a thickness of the adhesive layer measured in the bridge is greater than a thickness of the adhesive layer measured within one of the first petal and the second petal;

wherein a distance between adjacent lines in the embossed pattern of lines, measured along the outermost radial edge, increases in a direction from a location within the bridge toward the first petal.

11. The ostomy wafer of claim 1, wherein the plurality of petals comprises a first petal and a second petal and a third petal, with the first portion of the outer periphery of the wafer being concave and formed by a first bridge located between the first petal and the second petal, and a second portion of the outer periphery of the wafer being concave and formed by a second bridge located between the second petal and the third petal.

12. The ostomy wafer of claim 1, wherein the outer periphery of the ostomy wafer is non-circular, and the non-circular outer periphery of the ostomy wafer is formed by a plurality of petals each having a convex apex and a plurality or bridges;

wherein each bridge is connected between two of the plurality of petals;

wherein each bridge forms a concave portion of the outer periphery of the ostomy wafer.

13. The ostomy wafer of claim 1, wherein the distance between adjacent lines in the embossed pattern of lines, measured along the outer periphery of the ostomy wafer, increases in the direction from the location within each of the plurality of bridges toward one of the adjacent petals of the plurality of petals.

* * * * *